United States Patent [19] [11] 4,115,468
Antonov et al. [45] Sep. 19, 1978

[54] METHOD FOR DIMERIZATION OF OLEFINS

[76] Inventors: Andrei Alexandrovich Antonov, Profsojuznaya ulitsa 87, korpus 3, kv. 85; Viktor Alexandrovich Kabanov, Lomonosovsky prospekt 14, kv. 108; Marina Alexandrovna Martynova, ulitsa Stasovoi 4, kv. 34; Nikolai Sergeevich Nametkin, Leninsky prospekt 13, kv. 11; Stanislav Konstantinovich Pluzhnov, pereulok Yazykovsky 5, kv. 104; Vladimir Ivanovich Smetanjuk, ulitsa Stasovoi 4, kv. 34, all of Moscow, U.S.S.R.

[21] Appl. No.: 779,084

[22] Filed: Mar. 18, 1977

[51] Int. Cl.$^2$ ............................................. C07C 3/10
[52] U.S. Cl. ..................... 260/683.15 D; 252/429 B
[58] Field of Search .............................. 260/683.15 D; 252/429 B

[56] References Cited

U.S. PATENT DOCUMENTS 3,737,474  6/1973  Dunn ..................... 260/683.15 D
3,872,026  3/1975  Dunn ..................... 252/429 B

*Primary Examiner*—C. Davis
*Attorney, Agent, or Firm*—Lackenback, Lilling & Siegel

[57] ABSTRACT

A method for dimerization of olefins with a number of carbon atoms of at most 10 which comprises intermixing, in a medium of solvents selected from the group consisting of hydrocarbon solvents and halogenated hydrocarbon solvents at a temperature ranging from −20° to +100° C under a pressure of from 1 to 45 atm, of at least one of said olefines with a two-component catalyst consisting of an organoaluminum compound of the formula $R_nAlX_{3-n}$, wherein R is an alkyl with a number of carbon atoms of at most 8, X is a halogen, $n = 1$ or 2, and a graft-copolymer, swellable in said solvents, of a rubber selected from the group consisting of natural, synthetic carbo-chain and vinyl-containing siloxane rubbers, with vinylpyridine; said copolymer containing 0.5 to 40% by weight of polyvinylpyridine fragments complexed with a nickel salt; molar ratio between said organoaluminum compound and said nickel salt ranging from 1:1 to 100:1. In the method according to the present invention use is made of a catalyst with a maximal number of working active centers thus making it possible to substantially increase the process rate (for example, the rate of dimerization of propylene is about 9 kg of the product per gram of Ni per hour). The method can be performed under both batch and continuous operation conditions.

9 Claims, No Drawings

METHOD FOR DIMERIZATION OF OLEFINS

The present invention relates to petrochemistry and, more specifically, to methods for dimerization of olefins. The resulting olefins might be employed as monomers and co-monomers in the production of polyolefins, as stock feed for the preparation of monomers in the production of synthetic rubber, etc.

Known in the art are methods for dimerization of olefins by way of intermixing olefins with different homogeneous or heterogeneous catalysts.

Homogeneous catalysts consisting of an organoaluminium compound and a compound of a transition metal with low-molecular ligands containing elements of Groups V or VI of the periodic system (nitrogen, oxygen, phosphorus or sulfur) have certain disadvantages. Most important of said disadvantages reside in the difficulty in isolating the target products in pure form, since special methods are required for separation of the components present in the same phase; The difficulty in providing continuous processes — as a rule, all prior art methods are periodic ones. Furthermore, homogeneous catalysts are relatively unstable with time and cannot be regenerated.

The use of heterogeneous catalysts makes it possible to perform processes of dimerization of olefins both continuously and batch wise. However, in the operation with heterogeneous catalysts only a portion of active centers are employed and the process rate substantially depends on the catalyst structure and specific surface area. Moreover, during intermixing or displacement of the reaction mass the catalyst disintegration occurs, wherefore substantial losses thereof are observed.

Known in the art is a method for dimerization of olefins containing at most 12 carbon atoms by intermixing, in a medium of hydrocarbon or halogenated hydrocarbon solvents at a temperature of from $-50°$ to $+150°$ C under a pressure of from 1 to 100 atm, of at least one of said olefins with a two-component catalyst consisting of an organoaluminum compound of the formula: $R_nAlX_{3-n}$ wherein R is an alkyl with at most 12 carbon atoms, X is a halogen, $n = 1$ or 2, and a copolymer of vinylpyridine with a polyvinylsubstituted aromatic compound (such as divinylbenzene, trivinylbenzene); said copolymer contains 75 to 90% by weight of polyvinylpyridine fragments complexed with a nickel salt of an organic or inorganic acid; the molar ratio between the organoaluminum compound and the nickel salt ranges from 1:1 to 100:1.

The catalysts as employed in the prior art method are insoluble in the reaction medium; they feature the same disadvantages which are inherent in heterogeneous catalysts and, in the first place, the necessity of depositing the catalyst onto a porous material possessing a high specific surface area. Such a catalyst makes it possible to perform the process at a relatively low rate (for example, the rate of propylene dimerization is about 1.6 kg of the product per gram of nickel per hour).

It is an object of the present invention to provide a method for dimerization of olefins containing at most 10 carbon atoms, wherein use would be made of a catalyst, stable under the process conditions, with a maximal number of working active centers which could substantially increase the process rate.

It is another object of the present invention to provide a method for dimerization of diolefins which could be performed both periodically and continuously.

These and other objects of the present invention are accomplished by a method, wherein mixing in a medium of hydrocarbon or halogenated hydrocarbon solvents is performed at a temperature within the range of from $-20°$ to $+100°$ C, preferably from $0°$ to $70°$ C, under a pressure ranging from 1 to 45 atm, preferably from 1 to 10 atm, at least one of said olefins with a two-component catalyst consisting of an organoaluminum compound of the formula: $R_nAlX_{3-n}$, wherein R is an alkyl with at most 8 carbon atoms, X is a halogen, $n$ is 1 or 2, and a graft copolymer of natural, synthetic carbo-chain or vinylcontaining siloxane rubber with vinylpyridine swelling in said solvents, said copolymer containing 0.5 to 40% by weight of vinylpyridine fragments complexly bonded to a nickel salt; molar ratio of the organoaluminum compound to nickel salt ranges from 1:1 to 100:1, preferably from 1:1 to 10:1.

The catalyst employed in the method according to the present invention comprises a gel swellable, but insoluble, in the reaction medium and permeated over its entire volume with respect to both the starting olefin and the reaction products. This feature of the catalyst results in a substantially increased number of working active catalysis centers and, consequently, in an increased process rate (for example, the dimerization rate in the case of propylene is about 9 kg of the product per gram of nickel per hour).

In contrast to the prior art heterogeneous catalysts, the gel-like catalyst employed in the method according to the present invention does not disintegrate, it can be readily regenerated and used in the process for a long time without losing its original activity.

The catalyst according to the present invention features a higher activity, selectivity and increased specificity as compared to the prior art catalytic systems. The products of dimerization of olefins contain practically no trimers or higher oligomers. In the process of ethylene dimerization a content of butene-1 in the resulting mixture of butenes as high as 45% can be obtained. Products of propylene dimerization mainly consist of methylpentenes.

The method of dimerization of olefines with a number of carbon atoms of at most 10 according to the present invention is performed by intermixing at least one of said olefins with a catalyst in a medium of hydrocarbon solvents (such as aliphatic aromatic hydrocarbons) or halogenated hydrocarbon solvents at a temperature ranging from $-20°$ to $+100°$ C, preferably from $0°$ to $70°$ C under a pressure of from 1 to 45 atm preferably from 1 to 10 atm in reactors of a batch type (under stirring) or in dynamic continuous-flow tubular reactors. In the dimerization method according to the present invention use is made of both individual olefins (such as ethylene, propylene, butene) and mixtures thereof (such as a mixture of ethylene with propylene)

As a catalyst in the method according to the present invention use is made of a two-component catalyst consisting of an organoaluminum compound of the above-mentioned generic formula and a graft-copolymer of natural, synthetic carbo-chain or vinyl-containing siloxane rubber with vinylpyridine swelling in the above-mentioned solvents; said copolymer contains 0.5 to 40% by weight of polyvinylpyridine fragments complexed with a nickel salt of an organic or inorganic acid; molar ratio between the organoaluminum compound and nickel salt ranges from 1:1 to 100:1, preferably from 1:1 to 10:1.

To prepare the catalyst according to the present invention as the organoaluminum compound use is made of methylaluminum dichloride, dimethylaluminum chloride, ethylaluminum dichloride di-n-butylaluminum chloride, di-isobutylaluminum chloride, diheptylaluminum chloride and the like, preferably ethylaluminum dichloride and di-isobutylaluminum chloride.

Futhermore, to prepare the catalyst according to the present invention, as the synthetic carbo-chain rubber use is made, for example, of 1,2-polybutadiene, ternary copolymers of ethylene, propylene and a non-conjugated diene (such as ethylidene-norbornene, dicyclopentadiene, 1,5-hexadiene), cis-polybutadiene, isoprene rubber; preferably 1,2-polybutadiene.

As the nickel salt of an organic or inorganic acid to be used in the preparation of the catalyst according to the present invention use is made, for example, of nickel dichloride, nickel dibromide, nickel oleate, nickel acetylacetonate.

The above-mentioned graft-copolymer is prepared by the radical-type graft-copolymerization of 60–99.5% by weight of the above-mentioned rubber with 0.5 to 40% by weight of vinylpyridine such as 4-vinylpyridine, 2-vinylpyridine, 3-vinylpyridine, 2-methyl-5-vinylpyridine in a medium of hydrocarbon solvents or halogenated hydrocarbon solvents at a temperature of from 40° to 70° C. As the radical copolymerization initiators use is made, for example, of azo-bis--isobutyronitrile. On completion of the copolymerization the resulting copolymer is subjected to cross-linking by means of peroxide initiators such as benzoyl peroxide.

The thus-prepared copolymer is further reacted with the nickel salt in a medium of the above-mentioned solvents at a temperature within the range of from 10° to 50° C. As a result, a graft-copolymer containing 0.5 to 40% by weight of polyvinylpyridine fragments complexed with the nickel salt is obtained; this copolymer is swellable in the above-mentioned solvents. The resulting nickel-containing copolymer is thoroughly washed with the solvent to remove possible traces of the unreacted nickel salt.

The nickel-containing copolymer is then maintained in the reactor in a medium of an absolute hydrocarbon or halogenated hydrocarbon solvent. The copolymer swollen in the solvent is added, in a medium of an inert gas or in vacuum, an organoaluminum compound of the above-mentioned generic formula taken in such an amount that a molar ratio of the organoaluminum compound to the nickel salt is within the range of from 1:1 to 100:1, preferably from 1:1 to 10:1. After maintaining the reaction mixture at a temperature within the range of from 20° to 40° C for a period of from 30 to 40 minutes, the starting olefin or a mixture of olefins is fed into the reactor at a predetermined temperature and pressure of the dimerization process. However, the olefin can be added to the nickel-containing copolymer simultaneously with the organoaluminum compound.

The catalyst employed in the method according to the present invention is used in the form of granules swollen in the hereinabove-mentioned solvents and having a size of from 0.1 to 5 mm. These granules, unlike granules of conventional heterogenous catalysts, are readily permeable over the entire volume thereof in respect of molecules of the reactants and the resulting reaction products.

For a better understanding of the present invention, the following specific examples illustrating dimerization of olefins are given hereinbelow. Unless otherwise specified, in all the examples the molar ratio between said organoaluminum compound and nickel salt is referred to as the molar ratio of Al/Ni.

EXAMPLE 1

Into a 75 ml ampule there is added 1 g of synthetic carbo-chain rubber (a ternary copolymer of ethylene, propylene and dicyclopentadiene, unsaturation of which is 1.96 mol.%), 0.11 g of 4-vinylpyridine and 40 ml of heptane. After dissolvtion of the rubber, the solution is outgassed and added with 0.04 g of azo-bis-isobutyronitrile in 5 ml of benzene. The ampule is maintained for 10 hours at the temperature of 70° C. Thereafter the ampule contents is added with 0.04 g of benzoyl peroxide in 5 ml of benzene. The ampule is maintained at the temperature of 80° C for 10 hours. The resulting graft-copolymer of the rubber with 4-vinylpyridine is filtered-off, twice washed with small portions (by 10 ml each) of benzene and dried in vacuum. Said copolymer swells in hydrocarbon and halogenated hydrocarbon solvents. The content of poly-4-vinylpyridine fragments in the copolymer is 9% by weight.

The thus-prepared graft-copolymer in the amount of 0.1 g in the form of granules of a size of 2–3 mm is charged into a 100 ml glass reactor provided with a stirrer. The reactor is charged also with 0.01 g of nickel acetylacetonate and 40 ml of heptane. The reaction mixture is stirred for 20 hours at the temperature of 20° C. Thereafter, polymeric granules are washed several times (4–6 times) with heptane portionwise (by portions of 10 ml each) to remove the unreacted nickel acetylacetonate and dried in vacuum. As a result, a graft-copolymer containing poly-4-vinylpyridine fragments complexed with molecules of nickel acetylacetonate nickel-containing copolymer is obtained. The content of nickel in the copolymer is 1.2% by weight.

Into a reactor containing 0.1 g of said copolymer 0.5 ml of a 0.5M solution of di-isobutylaluminum chloride in absolute heptane (molar ratio of Al/Ni is about 10:1) is charged along with 10 ml of absolute heptane. The mixture is stirred for 0.5 hour at the temperature of 40° C, whereafter ethylene is fed into the reactor. The reaction is conducted at the temperature of 40° C under the pressure of 2 atm. After one hour the admission of ethylene is discontinued, the resulting dimers of ethylene are distilled off and collected in a receiver 9.5 g of butenes consisting of 37% by weight of butene-1 26% by weight of cis-butene-2 and 37% by weight of cis-butene-2 are thus obtained.

EXAMPLE 2

Into a 40 ml glass reactor provided with a stirrer, there is charged 0.1 g of a nickel-containing polymer prepared in a manner similar to that described in the foregoing Example 1, 0.5 ml of a 0.5M solution of di-isobutylaluminum chloride in absolute heptane and 10 ml of absolute heptane. The mixture is stirred for 0.5 hour at the temperature of 40° C, whereafter propylene is admitted into the reactor. The dimerization process is conducted at the temperature of 40° C under the pressure of 2.5 atm. After 2 hours, admission of propylene is discontinued and the resulting hexenes are collected in a receiver. The process rate is 6 kg of hexenes per one g of Ni per hour.

The catalyst features a high stability with time. Thus, after 30 days of catalyst storage in an argon atmosphere, propylene is again fed into the reactor and the process is conducted under the conditions described hereinabove. The process rate remains unchanged.

With the use of a prior art heterogeneous polymeric catalyst (cf. U.S. Pat. No. 3,773,474 Cl.260-683, 15D) in the process of propylene dimerization performed under identical conditions (pressure, temperature, Ni-content in the catalyst, molar ratio of Al/Ni), the process rate is about 3 times as less as in the case of using the catalyst according to the present invention.

EXAMPLE 3

Into a 40 ml glass reactor provided with a stirrer, there is charged 0.1 g of granulated nickel-containing copolymer prepared in a manner similar to that described in the foregoing Example 1, 0.5 ml of a 0.5M solution of di-iso-butylaluminum chloride in absolute heptane and 10 ml of absolute heptane. The mixture is stirred for 0.5 hour at the temperature of 40° C whereafter an equimolar mixture of ethylene and propylene is fed into the reactor. The process of dimerization of the mixture of olefins is conducted at the temperature of 40° C under the pressure of 2.5 atm. After one hour the process is discontinued and a mixture of $C_4$-$C_6$ olefins is obtained in the amount of 4.5 g which contains about 30% by weight of $C_5$-olefins.

EXAMPLE 4

Into a 250 ml three-neck flask provided with a stirrer, an inlet pipe for supply of argon, and a reflux condenser 5 g of a synthetic carbo-chain rubber (ternary copolymer of ethylene, propylene and ethylidene-norbornene; unsaturation is 2.75 mol.%) in 50 ml of cyclohexane are charged and dissolved under stirring. Thereafter, purified argon is admitted into the reactor and the mixture is heated at reflux for 2 hours. The solution is cooled to 50° C and the flask contents is added with 0.45 g of 4-vinylpyridine and 0.015 g of azo-bis-isobutyronitrile in 2 ml of benzene. The mixture is maintained for 8 hours at the temperature of 70° C, whereafter 2 ml of a benzene solution containing 0.02 g of benzoyl peroxide are added into the flask and the mixture is maintained for 12 hours at the temperature of 70° C. As a result, a graft-copolymer of rubber with 4-vinylpyridine containing 10% by weight of poly-4-vinylpyridine fragments is obtained. Said copolymer swells in hydrocarbon and halogenated hydrocarbon solvents. 0.1 g of the resulting graft-copolymer in the form of a 2-3 mm size granules is charged into a 40 ml metal reactor provided with a stirrer. The reactor is set under vacuum and 10 ml of a benzenic solution of nickel oleate (0.032 g of nickel oleate) are added thereinto. The mixture is stirred at the temperature of 20° C for 20 hours; the granules are washed with benzene (5 times by portions of 10 ml each) and dried in the reactor (under vacuum). As a result, a graft-copolymer containing fragments of poly-4-vinylpyridine complexed with molecules of nickel oleate is obtained. Nickel content in the copolymer is 1.31% by weight.

Thereafter, into the reactor containing granules of the copolymer mentioned hereinabove there are added, in an atmosphere of argon, 2 ml of a 0.5M solution of di-isobutylaluminum chloride in absolute heptane (molar ratio of Al/Ni is 40) and 10 ml of absolute heptane. Ethylene is supplied into the reactor at the temperature of 20° C under the pressure of 10 atm. As a result of the reaction, temperature is increased to 30° C and the process is further conducted at this temperature. After one hour the reaction is stopped and the reaction products are collected in the receiver. There are obtained 24 g of a mixture of butenes.

The catalyst employed in the process features a high stability with time. After 30 days of the catalyst storage in the atmosphere of argon, ethylene is again fed into the reactor and dimerization is conducted at the temperature of 30° C under the pressure of 6 atm. After one hour ethylene admission is discontinued and 15 g of a mixture of butenes are obtained.

EXAMPLE 5

Into an ampule 1 g of 1,2-polybutadiene is placed and reacted with 4-vinylpyridine under the conditions similar to those described in Example 1 hereinbefore. As a result, a graft-copolymer of 1,2-polybutadiene with 4-vinylpyridine is containing 15% by weight of poly-4-vinylpyridine fragments is obtained. The copolymer swells in hydrocarbon and halogenated hydrocarbon solvents is obtained.

Into a 50 ml flask provided with a stirrer there are charged 0.5 g of the thus-prepared copolymer in the form of granules with a size of 0.5 to 4 mm, 0.04 g of nickel acetylacetonate and 30 ml of heptane. The mixture is stirred for 20 hours at the temperature of 20° C, whereafter it is treated in the Soxhlet apparatus to remove the unreacted nickel acetylacetonate; the thus-obtained nickel-containing copolymer is dried in vacuum. The content of Ni in the copolymer is 1.56% by weight.

Into a tubular reactor the resulting nickel-containing copolymer is charged in the absence of air 2 ml of a 0.5M solution of di-isobutyl aluminum chloride in absolute heptane (molar ratio of Al/Ni is 6:1) and 30 ml of absolute heptane are added thereto. Thereafter, ethylene is fed into the reactor. Dimerization is conducted at the temperature of 20° C under the pressure of 2 atm. The dimerization products are collected into a collecting vessel. A mixture of butenes having the following composition: 45% of butene-1, 39% of trans-butene-2 and 16% of cis-butene-2 is obtained.

EXAMPLE 6

Under the conditions described in the foregoing Example 5 with the use of the same catalyst, dimerization of propylene is conducted under the pressure in the system of 2.6 atm to give a mixture of hexenes having the following composition 8% of 4-methylpentene-1, 12% of cis-4-methylpentene-2, 55% of trans-4-methylpentene-2, 20% of a mixture of 2-methylpentene-1 and cis- and trans-2-methyl-pentene-2; the amount of other hexenes is 5%.

EXAMPLE 7

Into an ampule there is placed 1 g of a siloxane rubber containing 2% of vinyl groups and this rubber is reacted with 4-vinylpyridine under the conditions similar to those described in Example 1 hereinbefore. As a result, there is obtained a graft-copolymer of the siloxane rubber with 4-vinylpyridine containing 20% by weight of poly-4-vinylpyridine fragments; this copolymer swells in hydrocarbon and halogenated hydrocarbon solvents.

Into a reactor provided with a stirrer there is charged 0.1 g of the thus-prepared copolymer in the form of granules with a size of 2 to 5 mm, 0.01 g of nickel nitrate and 20 ml of heptane. The mixture is stirred for 20 hours at the temperature of 20° C, whereafter the granules are washed several times with small portions of heptane and the nickel-containing copolymer is dried in vacuum. The content of Ni in the copolymer is 1.5% by weight.

Into a reactor with the nickel-containing copolymer in the atmosphere of argon there are added 4 ml of a 0.5M solution of di-isobutylaluminum chloride in absolute heptane (molar ratio of Al/Ni is 77) and 15 ml of absolute heptane. The mixture is stirred for 0.5 hour at the temperature of 10° C and ethylene is fed thereinto. The reaction is conducted at the temperature of 10° C under the pressure of 2 atm. After 2 hours admission of ethylene is discontinued and the resulting dimerization products are collected in a receiver. A mixture of butenes having the following composition: 36% of butene-1, 22% of cis-butene-2 and 4% of trans-butene-2 is obtained.

EXAMPLE 8

Into an ampule there is charged 1 g of natural rubber which is reacted with 4-vinylpyridine under the conditions similar to those described hereinabove in Example 1. As a result, a graft-copolymer of natural rubber with 4-vinylpyridine containing 13% by weight of poly-4-vinylpyridine fragments is obtained, the copolymer swells in hydrocarbon and halogenated hydrocarbon solvents.

Into a reactor provided with a stirrer there is charged 0.1 g of the resulting copolymer in the form of granules with a size of 0.1 to 3 mm, 0.01 g of nickel chloride and 20 ml of heptane. The mixture is stirred for 20 hours at the temperature of 20° C, whereafter the granules are washed several times with small portions of heptane and the nickel-containing polymer is dried in vacuum. Nickel content in the copolymer is 1.55% by weight.

Into a reactor with the nickel-containing copolymer there is added, in the absence of air, 0.25 ml of a 0.5M solution of ethylaluminum dichloride in absolute heptane (molar ratio of Al/Ni is about 2.5) and 10 ml of absolute heptane. The mixture is stirred for 0.5 hour and ethylene is then fed thereinto at the temperature of 60° C. The pressure in the system is 2 atm. After 2 hours ethylene feeding is stopped and the dimerization products are collected into a receiver. 18.7 g of a mixture of butenes are thus obtained.

EXAMPLE 9

Under the conditions of the foregoing Example 8 with the use of the same catalyst (molar ratio of Al/Ni is 1) dimerization of propylene is conducted in the medium of toluene under the pressure in the system of 2.5 atm. A mixture of hexenes containing mainly 4-methyl- and 2-methylpentenes is obtained.

EXAMPLE 10

Into a reactor provided with a stirrer there is charged 0.2 g of a graft-copolymer of a synthetic carbo-chain rubber (ternary copolymer of ethylene, propylene and dicyclopentadiene; unsaturation is 1.96 mol.%) with 4-vinylpyridine. The copolymer contains 5% by weight of poly-4-vinylpyridine fragments; this copolymer is prepared following the procedure described in Example 1 hereinbefore. Further charged into the reactor is 0.01 g of nickel acetylacetonate along with 40 ml of heptane. The mixture is stirred for 10 hours at the temperature of 20° C and then washed several times with small portions (by 10 ml each) of heptane. The resulting nickel-containing copolymer is dried in vacuum, whereafter 0.3 ml of a 0.5M solution of diheptylaluminium chloride in absolute heptane (molar ratio of Al/Ni is 8) and 15 ml of absolute heptane are added thereto. The mixture is stirred at the temperature of 40° C for 0.5 hour, whereafter ethylene is fed thereinto. The reaction is conducted at the temperature of 40° C under the pressure of 2 atm. After two hours, admission of ethylene is discontinued, the reaction products are distilled-off into a collecting vessel to give 21.2 g of butenes of the following composition; 39% of butene-1, 25% of cis-butene-2 and 26% of trans-butene-2,

EXAMPLE 11

Into a reactor provided with a stirrer there is charged 0.2 g of granules of a graft-copolymer of 1,2-polybutadiene with 4-vinylpyridine. The copolymer contains 40% by weight of poly-4-vinylpyridine fragments; the copolymer is prepared by the procedure described in Example 5 hereinbefore. Then, the reactor contents is added with 0.07 g of nickel acetylacetonate and 20 ml of heptane. The mixture is stirred for 15 hours at the temperature of 20° C and then washed with several small portions of heptane. The resulting nickel-containing copolymer is dried in vacuum, whereafter introduced into the reactor are 4 ml of a 0.5M solution of ethylaluminum dibromide in absolute heptane (molar ratio of Al/Ni is about 20) and 15 ml of absolute heptane. Simultaneously with addition of the organoaluminum compound, ethylene is fed into the reactor. The reaction is conducted at the temperature of 72° C under the pressure of 3 atm. After 2 hours the dimerization products are collected into a receiver. A mixture of butenes having the following composition; 35% of butene-1, 22% of cis-butene-2, 43% of trans-butene-2 is obtained.

EXAMPLE 12

Into a reactor provided with a stirrer there is charged 0.25 g of a graft-copolymer of 1,2-polybutadiene with 2-vinylpyridine. The copolymer contains 28% by weight of poly-2-vinylpyridine fragments; said copolymer is prepared by the procedure described in Example 5 hereinbefore. The reactor contents is further added with 0.07 g of nickel bromide and 20 ml of a mixed solvent (methanol-benzene 1:1). The mixture is stirred at the temperature of 20° C for 6 hours and then washed several times with small portions of said solvent. The resulting nickel-containing copolymer is dried in vacuum, whereafter the calculated amount of ethylaluminum dichloride (molar ratio of Al/Ni is 100:1) and 20 ml of benzyl chloride are added thereto. Simultaneously with incorporation of the organaluminum compound ethylene is charged into the reactor. The reaction is carried out under stirring at the temperature of 90° C under the pressure of 6 atm. One hour after the reaction is stopped, the dimerization products are collected into a receiver and subjected to analysis. A mixture of butenes having the same composition as in the previous Example 11 is obtained.

EXAMPLE 13

Dimerization of ethylene is conducted in the medium of n-butylbromide at the temperature of −20° C under the pressure of 1 atm in the presence of a catalyst similar to that employed in Example 1 (the content of poly-4-vinylpyridine fragments is 0.5% by weight, molar ratio of Al/Ni is 9). After two hours the reaction is stopped. There are obtained 3 g of a mixture of butenes having the following composition: 66% of butene-1, 13% of cis-butene-2 and 21% of trans-butene-2.

EXAMPLE 14

Into a reactor provided with a stirrer there is charged 0.12 g of granules of a nickel-containing copolymer similar to that described in Example 1, 0.5 ml of a 1.5M solution of diethylaluminum chloride in absolute pentane (molar ratio of Al/Ni is 30) and 50 ml of absolute pentane. The mixture is stirred for 0.5 hour at the temperature of 20° C, whereafter ethylene is fed into the reactor. The reaction is conducted at the temperature of 20° C under the pressure of 2 atm. In 3 hours admission of ethylene is discontinued. Rate of dimerization is 6.5 kg of butenes per gram of Ni per hour. After 20 hours the liquid contained in the reactor is distilled off in vacuum at the temperature of 20° C. 50 ml of absolute pentane are added into the reactor and then ethylene is fed thereinto. Dimerization reaction is conducted at the temperature of 20° C under the pressure of 2 atm for 3 hours. Said succession of operations (dimerization and subsequent removal of liquid from the reactor) is repeated for the period of 100 days.

At the experiment's end the dimerization rate is 5.9 kg of butenes per gram of Ni per hour. The mixture of butenes has the following composition: 33% of butene-1, 24% of cisbutene-2, and 43% of trans-butene-2.

EXAMPLE 15

Dimerization of propylene is conducted in the medium of chlorobenzene at the temperature of 30° C under the pressure of 2 atm in the presence of a catalyst similar to that employed in Example 1 hereinbefore (the content of poly-4-vinylpyridine fragments in the copolymer is 15% by weight; molar ratio of Al/Ni is 7). After one hour the reaction is discontinued and the dimerization products are isolated from the reaction mixture to give 11.5 g of $C_6$-olefins consisting mainly of methylpentenes (dimerization rate is about 9 kg of the product per gram of Ni per hour).

EXAMPLE 16

Dimerization of ethylene is conducted in the medium of heptane at the temperature of 0° C under the pressure of 1.5 atm in the presence of a catalyst similar to that employed in Example 5 hereinbefore (molar ratio of Al/Ni is 9). After one hour the reaction is stopped. 5.5 g of a mixture of butenes are obtained which has the following composition: 38% of butene-1, 26% of cis-butene-2 and 36% of trans-butene-2.

EXAMPLE 17

Dimerization of propylene is conducted in the medium of decane at the temperature of 100° C under the pressure of 16 atm in the presence of a catalyst prepared in a manner similar to that described in Example 5 and consisting of 0.1 g of a granulated nickel-containing copolymer 1,2-polybutadiene with 4-vinylpyridine (content of poly-4-vinylpyridine is 15% by weight) and ethylaluminum dichloride (molar ratio of Al/Ni is 5). After two hours the reaction is discontinued to give 6.2 g of a mixture of $C_6$-olefins consisting mainly of 4- and 2-methylpentenes.

EXAMPLE 18

Dimerization of ethylene is conducted in a metallic reactor in the medium of heptane at the temperature of 30° C under the pressure of 22 atm in the presence of a catalyst similar to that employed in the foregoing Example 5 (molar ratio of Al/Ni is 6). The reaction is stopped after 0.5 hour to give a mixture of butenes (19.3 g) of the following composition: 37% of butene-1, 26% of cis-butene-2 and 37% of trans-butene-2.

EXAMPLE 19

Dimerization of ethylene is conducted in a metallic reactor in the medium of heptane at the temperature of 20° C under the pressure of 45 atm in the presence of a catalyst similar to that employed in Example 5 (molar ratio of Al/Ni is 6). The reaction is stopped after 0.5 hour to give 36.2 g of a mixture of butenes.

EXAMPLE 20

Ethylene is subjected to dimerization in a metallic reactor in the medium of heptane at the temperature of 20° C under the pressure of 27 atm in the presence of a catalyst similar to that employed in Example 5 hereinbefore (molar ratio of Al/Ni is 6). The reaction is discontinued after 0.5 hour to give 21.3 g of a mixture of butenes.

EXAMPLE 21

Charged into a reactor is 0.1 g of granules of a nickel-containing copolymer similar to that employed in Example 1 (the content of poly-4-vinylpyridine fragments is 9% by weigh In the absence of air and humidity added thereto is 0.5 ml of a 0.5M solution of ethylaluminum dichloride in chlorobenzene (molar ratio of Al/Ni is 10), 15 ml of chlorobenzene and 6.5 g of butene-1. The reaction is conducted at the temperature of 30° C. After one hour the reaction is discontinued. The dimerization product, i.e. $C_6$-olefins, is isolated by a conventional method. The dimerization rate is about 4 kg of the product per one g of Ni per hour.

In a similar manner, making use of the catalysts described in the foregoing Examples 1 through 21 under the conditions of Example 21 dimerization is conducted with other individual olefins ($C_5$–$C_{10}$ olefins) or different mixtures of olefines; dimerization rates obtained therewith vary within the range of from 3 to 5 kg of the product per gram of Ni per hour.

What is claimed is:

1. A method for dimerization of olefins having up to 10 carbon atoms, which comprises: intermixing at least one of said olefins with a two-component catalyst in a medium of solvents selected from the group consisting of hydrocarbon solvents and halogenated hydrocarbon solvents at a temperature ranging from −20° to +100° C at a pressure of from 1 to 45 atmospheres, said two-component catalyst consisting of an organoaluminum compound of the formula $R_nAlX_{3-n}$, wherein R is an alkyl having up to eight carbon atoms, X is a halogen, i n equals 1 or 2; and a graft-copolymer swellable in said solvents, of a rubber selected from the group consisting of natural, synthetic carbo-chain and vinyl-containing siloxane rubbers, with vinylpyridine; said copolymer containing 0.5 to 40% by weight of polyvinylpyridine fragments complexed with a nickel salt; the molar ratio between said organometallic compound and said nickel salt ranging from 1:1 to 100:1.

2. The method of claim 1 wherein the intermixing of said olefins with said catalyst is conducted at a temperature ranging from 0° to 70° C at a pressure of from 1 to 10 atmospheres.

3. The method of claim 1, wherein the two-component catalyst consists of:

(a) an organoaluminum compound selected from the group consisting of ethylaluminum dichloride and di-isobutylaluminum chloride; and (b) a graft-copolymer swellable in said solvents, of a synthetic carbo-chain rubber with 4-vinylpyridine; said copolymer containing 0.5 to 40% by weight of poly-4-vinylpyridine fragments complexed with a nickel salt selected from the group consisting of nickel dichloride and nickel acetylacetonate; the molar ratio between said organoaluminum compound and said nickel salt ranging from 1:1 to 10:1.

4. The method of claim 3, wherein the graft-copolymer of a synthetic carbo-chain rubber with vinylpyridine consists of 1,2-polybutadiene with 4-vinylpyridine.

5. The method of claim 1, wherein said catalyst is employed in the form of granules.

6. The method of claim 5, wherein said granules vary in size from 0.1 to 5 millimeters.

7. A dimerization catalyst consisting of an organoaluminum compound of the formula $R_n AlX_{3-n}$, wherein R is an alkyl having up to 8 carbon atoms, X is a halogen, $n = 1$ or 2; and a graft-copolymer, swellable in said solvents, of a rubber selected from the group consisting of natural, synthetic carbo-chain and vinyl-containing siloxane rubbers, with vinylpyridine; said copolymer containing 0.5 to 40% by weight of polyvinylpyridine fragments complexed with a nickel salt; the molar ratio between said organometallic compound and said nickel salt ranging from 1:1 to 100:1.

8. The catalyst of claim 7, wherein said components consist of:

(a) an organoaluminum compound selected from the group consisting of ethylaluminum dichloride and di-isobutylaluminum chloride; and (b) a graft-copolymer, swellable in said solvents, of a synthetic carbo-chain rubber with 4-vinylpyridine; said copolymer containing 0.5 to 40% by weight of poly-4-vinylpyridine fragments complexed with a salt of nickel selected from the group consisting of nickel dichloride and nickel acetylacetonate; the molar ratio between said organoaluminum compound and said nickel salt ranging from 1:1 to 10:1.

9. The catalyst of claim 7, wherein the graft-copolymer of a synthetic carbo-chain rubber with vinylpyridine is 1,2-polybutadiene with 4-vinylpyridine.

* * * * *